United States Patent
Yoon et al.

(10) Patent No.: US 12,016,833 B2
(45) Date of Patent: Jun. 25, 2024

(54) COMBINATION FORMULATION CONTAINING COLCHICINE FOR TREATMENT OR ENHANCING THE THERAPY OF LIVER DISEASE

(71) Applicant: ACEBiomed, Inc., Jinju (KR)

(72) Inventors: Ju Ho Yoon, Seoul (KR); Wang Jo Cha, Gwacheon (KR); Sun Ah Ham, Changwon (KR)

( * ) Notice: Subject to any disclaimer, the term of this patent is extended or adjusted under 35 U.S.C. 154(b) by 291 days.

(21) Appl. No.: 17/061,583

(22) Filed: Oct. 2, 2020

(65) Prior Publication Data

US 2021/0220296 A1 Jul. 22, 2021

(30) Foreign Application Priority Data

Jan. 22, 2020 (KR) .................. 10-2020-0008258

(51) Int. Cl.
  *A61K 31/165*  (2006.01)
  *A61K 31/155*  (2006.01)
  *A61P 1/16*    (2006.01)

(52) U.S. Cl.
  CPC .......... *A61K 31/165* (2013.01); *A61K 31/155* (2013.01); *A61P 1/16* (2018.01)

(58) Field of Classification Search
  CPC ........ A61K 31/165; A61K 31/155; A61P 1/16
  See application file for complete search history.

(56) References Cited

U.S. PATENT DOCUMENTS

2008/0031964 A1* 2/2008 Messadek .............. A61K 31/14
                                                    424/490

FOREIGN PATENT DOCUMENTS

KR   10-2015-0102969 A   9/2015
KR   10-2015-0143725 A   12/2015

OTHER PUBLICATIONS

Xu et al. "Metformin improves hepatic IRS2/PI3K/Akt signaling in insulin-resistant rats of NASH and cirrhosis," J. Endocrinology, 2016, vol. 229, pp. 133-144 (Year: 2016).*
Demidowich et al. Colchicine to decrease NLRP3-activated inflammation and improve obesity-related metabolic dysregulation,"Medical Hypotheses," 2016, vol. 92, pp. 67-73 (Year: 2016).*
Chen et al. "NLRP3 inflammasome formation and activation in nonalcoholic steatohepatitis: Therapeutic target for antimetabolic syndrome remedy FTZ," Oxidative Medicine and Cellular Longevity, 2018, Article ID 2901871, https://doi.org/10.1155/2018/2901871 (Year: 2018).*

(Continued)

*Primary Examiner* — Shengjun Wang

(57) ABSTRACT

Exemplary embodiments of the present invention relate to a combination formulation for treatment or enhancing the therapy of liver disease, and more particularly, to a combination formulation prepared by containing colchicine and metformin as main active ingredients.

The composition according to exemplary embodiments of the present invention may be used as an effective therapeutic agent for liver disease capable of treating and preventing liver fibrosis, liver cirrhosis, liver cancer, or hepatitis by reducing the amount of fat accumulated in the liver tissues by a synergistic effect of colchicine and metformin and lowering glucose tolerance and insulin tolerance and further, may be used as an excellent drug capable of replacing ursodeoxycholic acid.

8 Claims, 10 Drawing Sheets

(56) References Cited

OTHER PUBLICATIONS

"Colchicine and Cysteine in the management of Paracetamolinduced Liver damage," Austine Ighorodje et al., International Journal of Pharmaceutical Science Invention, 8(1), pp. 18-24, Jan. 2019.

"Effect of Vitamin E or Metformin for Treatment of Nonalcoholic Fatty Liver Disease in Children and Adolescents," Joel Lavine, et al., The Journal of the American Medical Association, 305(16), pp. 1659-1668 (2011).

* cited by examiner

COMBINATION FORMULATION CONTAINING COLCHICINE FOR TREATMENT OR ENHANCING THE THERAPY OF LIVER DISEASE

CROSS-REFERENCE TO RELATED APPLICATIONS

This application claims priority from and the benefit of Korean Patent Application No. 10-2020-0008258, filed on Jan. 22, 2020, which is hereby incorporated by reference for all purposes as if fully set forth herein

BACKGROUND

Field

The present invention relates to a combination formulation for treatment or enhancing the therapy of liver disease, wherein the combination formulation is formed by containing colchicine and metformin as main active ingredients. More specifically, the present invention relates to a pharmaceutical composition that exhibits superior pharmacological effects than conventional drugs administered alone in the related art when colchicine, which is a drug known to have a liver protective effect in the related art, is mixed and administered with metformin, which is mainly used for diabetic disease, and to a pharmaceutical composition for enhancing the therapy of liver disease which is prepared by specifically limiting the contents of the drugs.

Discussion of the Related Art

The liver is a biological organ that plays a pivotal role in the metabolism of substances out of the body and in the body, and continuously undergoes enzymatic reactions and energy metabolism. Currently, among chronic diseases in Korea, hepatitis, liver cirrhosis, and liver cancer have the highest ratio with circulatory system diseases, and account for a large proportion of the causes of death from diseases. In particular, as the drinking population is larger, and the rate of liver damage caused by binge drinking is higher than in developed countries, the liver damage is of high interest. Continuous damage to liver tissues caused by viral infections or drinking has characteristics of disease that develop into liver cirrhosis or liver cancer. Considering the physiological characteristics and importance of the liver tissue, treatment and prevention of liver disease are very important, and there is a need to develop a pharmaceutical composition capable of reducing liver tissue damage and ultimately enhancing a therapy thereof.

In particular, liver fibrosis refers to a state in which a damaged liver tissue is transformed into a fibrous tissue such as collagen, rather than being repaired to normal hepatocytes, as part of a bioadaptation reaction accompanying chronic liver disease such as hepatitis. The liver fibrosis is a bio-adaptation reaction that occurs in the process of repairing tissue damage, but it is inevitable that liver functions deteriorate in a sense that the liver is replaced with fibrous tissues that cannot perform the intrinsic functions of a liver such as metabolism and bile secretion in vivo. The development of suitable therapeutic agents has been conducted as an important task in drug developments, in that the liver fibrosis phenomenon very often develops into liver cirrhosis, leading to death. Until now, however, since the mechanism of the liver fibrosis itself is not clearly known, no suitable therapeutic drug has been developed.

Meanwhile, colchicine has been widely used as a therapeutic agent for gout-related arthritis, and cases of successful treatment for acute gout and recurrent gout have been reported. In addition, the pharmacokinetic properties of colchicine have been also reported, and colchicine can be administered orally. For colchicine, it has been more than 10 years that cases for various indications have been reported, mechanism studies have been conducted, and colchicine has been reported to have effects on rheumatoid and non-rheumatic arthritis, prevention of amyloidosis in familial Mediterranean fever, prevention of fever, Behcet's disease, etc.

In addition, metformin (UDCA), which has been widely used as a therapeutic agent for liver disease, etc. in the related art, has a strong detoxifying ability as a main ingredient of the gall bladder of a bear and is known to activate the detoxification and metabolism of the liver and prevent cholesterol from being accumulated in the liver.

Most of the raw material for UDCA used in Korea has been imported from China. Recently, however, due to various environmental changes in China, diseases or the like are negatively affecting the animals that are the sources of UDCA raw material, which, as a result, limits the amount and price to be imported from China. Accordingly, there is an urgent need to develop drugs that can replace UDCA to treat liver disease and the like.

SUMMARY

The present invention has been derived to solve the above problems, and the present inventors have found that colchicine (which was a therapeutic agent for gouty arthritis) and metformin (which has been used as a therapeutic agent for metabolic diseases such as cardiovascular disease and diabetes in the related art) can be mixed, as the main active ingredients, and administered in combination to enhance the therapy of liver fibrosis or inflammatory liver disease, and completed the present invention based thereon.

Another object of the present invention is to provide a dose exhibiting the most suitable efficacy in administering colchicine and metformin into the human body.

The objects of the present invention to be achieved are not limited to the aforementioned objects, and other objects, which are not mentioned above, will be apparently understood to those skilled in the art from the following description.

To achieve the objects of the present invention, exemplary embodiments of the present invention provide a combination formulation for the treatment of liver disease containing colchicine and metformin as main active ingredients.

Exemplary embodiments of the present invention provide a pharmaceutical composition for enhancing the therapy of liver disease comprising colchicine and metformin as main active ingredients. The pharmaceutical composition for enhancing the therapy is the same concept as a therapeutic aid for preventing and treating liver disease or the like, which is one of the target diseases of the present invention.

In one embodiment of the present invention, the liver disease may be at least one selected from liver fibrosis, liver cirrhosis, liver cancer, and inflammatory liver disease.

In one embodiment of the present invention, co-administration may be in the form of administering the composition simultaneously, separately or sequentially with the liver protective agent.

In one embodiment of the present invention, the inflammatory liver disease may be selected from hepatitis, acute hepatitis, chronic hepatitis, alcoholic hepatitis, non-alcoholic hepatitis, subacute hepatitis, viral hepatitis, toxic liver disease, liver abscess, granulomatous hepatitis, autoimmune hepatitis, and lupus hepatitis.

The composition according to the present invention is a combination formulation formed by containing colchicine and metformin as main active ingredients, and the combination formulation provided in the present invention may enhance the therapy of liver fibrosis, inflammatory liver disease, or the like by co-administering drugs exhibiting a synergistic effect.

The combination formulation according to the present invention may be effectively used as a pharmaceutical composition for enhancing the therapy of liver disease such as liver fibrosis, liver cirrhosis, liver cancer or inflammatory liver disease including hepatitis, even when administered in a low dose.

DETAILED DESCRIPTION OF EMBODIMENTS

Figure 1:
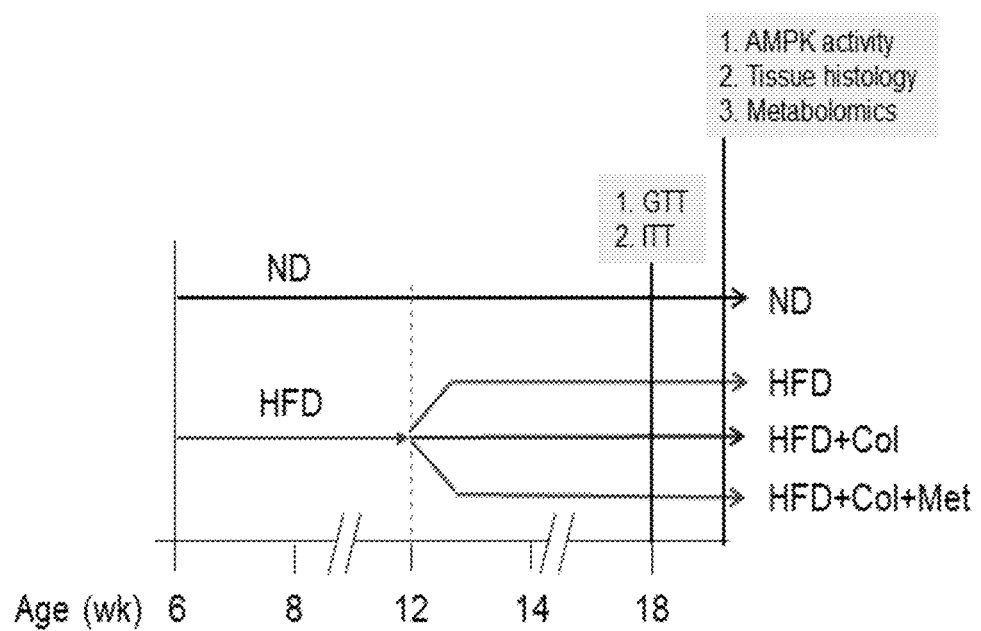
FIG. 1 shows an overall process to practice an exemplary embodiment of the present invention.

The present inventors have found that a combination formulation containing both colchicine and metformin in accordance with embodiments of the present invention improved liver functions in patients with severe chronic active hepatitis, severe disease activity, and early liver cirrhosis, when administered to them. In addition, the present inventors have found that colchicine combined with or used in combination with a liver protective agent enhanced treatment, when administered, and completed the present invention based thereon.

Hereinafter, exemplary embodiments of the present invention will be described in detail.

The term "inflammatory liver disease" used in the present application is generally called hepatitis, and refers to an overall disease caused by inflammation of liver cells and liver tissue. The inflammatory liver disease according to embodiments of the present invention may include hepatitis, acute hepatitis, chronic hepatitis, alcoholic hepatitis, non-alcoholic hepatitis, subacute hepatitis, viral hepatitis, toxic liver disease, liver abscess, granulomatous hepatitis, autoimmune hepatitis, lupus hepatitis, etc., but is not limited thereto.

The term "treatment" used in the present application refers to any act of improving or beneficially altering liver fibrosis or inflammatory liver disease by administration of the pharmaceutical composition according to embodiments of the present invention.

Colchicine, which is a main active ingredient used in exemplary embodiments of the present invention, is a substance extracted from plants of the genus *Colchicum*, and a drug which is mainly used as an alternative drug for gout when a nonsteroidal anti-inflammatory agent does not smoothly show on the therapy for gout, and is also used to treat familial Mediterranean fever, pericarditis, and Behcet's disease.

Metformin, which is another active ingredient used in exemplary embodiments of the present invention, is a biguanide drug and a drug that has an effect of improving blood sugar and is mainly used as a therapeutic agent for diabetes. The action mechanism of metformin is not known precisely, but is believed to inhibit cellular respiration occurring in the mitochondria and activate AMPK to prevent an increase in concentration of cAMP induced by glucagon, and consequently inhibit the activity of PKA to inhibit the production of glucose.

The present inventors have confirmed through various experiments that the efficacy of treating liver disease was enhanced when colchicine and metformin were administered in combination.

In accordance with one embodiment of the present invention, the recovery of an albumin level and a total protein concentration was confirmed based on a blood biochemical test where a combination formulation of colchicine and metformin was administered in comparison with administration of colchicine alone. Also, it was confirmed that the activation of AMP-activated protein kinase (AMPK) and acetyl-CoA carboxylase (ACC) was further increased.

In addition, in one embodiment of the present invention, as a result of confirming fibrin levels by a hydroxyproline assay, when colchicine and metformin were administered in a combination formulation, as compared to administration of colchicine alone, the reduction of the fibrin levels was confirmed in the co-administration.

In addition, in one embodiment of the present invention, as a result of confirming changes in liver functions and liver tissues by a histopathological examination and H&E staining, when colchicine and metformin were administered in a combination formulation, as compared to administration of colchicine alone, further improvement of a pathology was confirmed in the co-administration.

The contents of colchicine and metformin contained in a combination formulation in accordance with embodiments of the present invention are as follows.

When administering the combination formulation in accordance with embodiments of the present invention, one may use the content of colchicine of 10 to 200 μg/kg, more specifically 50 to 100 μg/kg and the content of metformin of 50 to 400 mg/kg, more specifically 100 to 200 μg/kg.

When the content of colchicine is less than 10 μg/kg, the efficacy of colchicine may be rarely exhibited, and when the content thereof is more than 200 μg/kg, there may be side effects of causing gastrointestinal disorders when administered.

When the content of metformin is less than 50 mg/kg, the efficacy may not be exhibited, and when the content thereof is more than 400 mg/kg, there may be side effects such as abdominal pain, diarrhea, and vomiting.

When the content of metformin is less than 10 mg/kg, the efficacy may not be exhibited, and when the content thereof is more than 50 mg/kg, side effects such as gastrointestinal disorders may occur.

The term "combination formulation" used in the present application refers to a pharmaceutical composition provided according to embodiments of the present invention.

The composition according to embodiments of the present invention may further include suitable carriers, excipients and diluents, which are commonly used in the preparation of the pharmaceutical composition. In addition, according to general methods, the composition may be formulated and used in the form of oral formulations such as powders, granules, tablets, capsules, suspensions, emulsions, syrups, and aerosols, external preparations, suppositories and sterile injectable solutions, and may also be formulated and used in the form of a unit-dosage form suitable for oral administration.

The carrier, the excipient, and the diluent which may be included in the composition include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, etc. When the composition is formulated, the formulation may be prepared by using a diluent or an excipient, such as a filler, an extender, a binder, a wetting agent, a disintegrating agent, and a surfactant which are generally used.

A solid formulation for oral administration includes a tablet, a pill, a powder, a granule, a capsule, and the like, and the solid formulation may be prepared by mixing at least one excipient, for example, starch, calcium carbonate, sucrose, lactose, gelatin, and the like with the composition. Further, lubricants such as magnesium stearate and talc may be used in addition to simple excipients. A liquid formulation for oral administration may correspond to a suspension, an oral liquid, an emulsion, a syrup, and the like, and may include various excipients, for example, a wetting agent, a sweetener, an aromatic agent, a preserving agent, and the like in addition to water and liquid paraffin which are commonly used as simple diluents. A formulation for parenteral administration includes a sterile aqueous solution, a non-aqueous solution, a suspension, an emulsion, a lyophilizing agent, and a suppository. As the non-aqueous solution and the suspension, propylene glycol, polyethylene glycol, vegetable oil such as olive oil, injectable ester such as ethyl oleate, and the like may be used. As a base compound of the suppository, witepsol, macrogol, tween 61, cacao butter, laurin, glycerogelatin, and the like may be used.

In addition, an antioxidant may be further added to the composition for the treatment of liver disease and the like provided in the present invention. As the antioxidant, compounds in Vitamin B group such as thiamin (vitamin B1), riboflavin (vitamin B2), niacin (vitamin B3), pantothenic acid (vitamin B5), pyridoxine (vitamin B6), and cobalamin (vitamin B12), vitamin C, vitamin D, vitamin E, etc. may be used.

The pharmaceutical composition according to embodiments of the present invention may be administered in a pharmaceutically effective dose. In the present application, the "pharmaceutically effective dose" refers to a sufficient amount to treat disease at a reasonable benefit/risk ratio applicable to medical treatment. An effective dose level may be determined according to elements including the type and severity of disease of a patient, activity of a drug, sensitivity to a drug, a time of administration, a route of administration, an emission rate, duration of treatment, and simultaneously used drugs, and other elements well-known in the medical field. The pharmaceutical composition according to embodiments of the present invention may be administered as a separate therapeutic agent or in combination with other therapeutic agents, and may be administered sequentially or simultaneously with conventional therapeutic agents, and may be administered singly or multiply. It is important to administer an amount capable of obtaining a maximum effect with a minimal amount without side effects by considering all the elements, which may be easily determined by those skilled in the art. The pharmaceutical composition according to embodiments of the present invention may be administered to a subject by various routes. All modes of administration may be expected, for example, the pharmaceutical composition may be administered by oral, rectal or intravenous, intramuscular, subcutaneous, intrathecal epidural or cerebrovascular injection. The pharmaceutical composition of the present invention may be determined according to a type of drug as an active ingredient in addition to many related factors, such as disease to be treated, the administration route, the age, gender, and weight of the patient, and the severity of the disease.

Hereinafter, Examples are presented in order to assist understanding of the present invention. However, the following Examples are just provided to more easily understand the present invention, but the contents of the present invention are not limited by the following Examples.

Example

1. Preparation of Experimental Animals and Experimental Methods

Six-week-old C57BL/6J male rats ingested a normal diet (ND) or a high fat diet (HFD) for 6 weeks, and then colchicine (10 μg/kg) alone was administered or colchicine (10 μg/kg)/metformin (50 mg/kg) was co-administered. The drugs were administered with a high fat diet for a total of 6 weeks, and administered by oral gavage 3 times a week.

FIG. 1 shows an overall process of preparing the animals and performing a test procedure for administration of colchicine alone and co-administration of colchicine/metformin.

Figure 2:
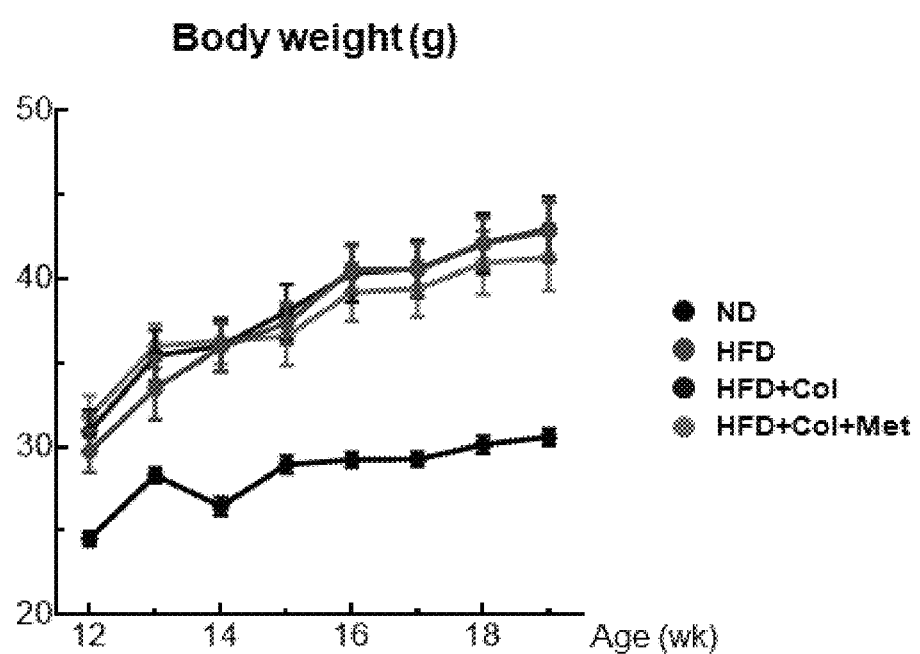
FIG. 2 illustrates changes in weights of rats when colchicine or colchicine/metformin was administered or co-administered to obesity-induced rats.

As illustrated in FIG. 2, when administration of colchicine alone and co-administration of colchicine/metformin were performed to rats whose weights gained on a high fat diet by the above method, there was no significant change in weights of the whole rats.

2-1. Pathologic Test of Liver Tissue when Administering Colchicine Alone and Co-Administering Colchicine/Metformin to Obesity-Induced Rats.

Figure 3:
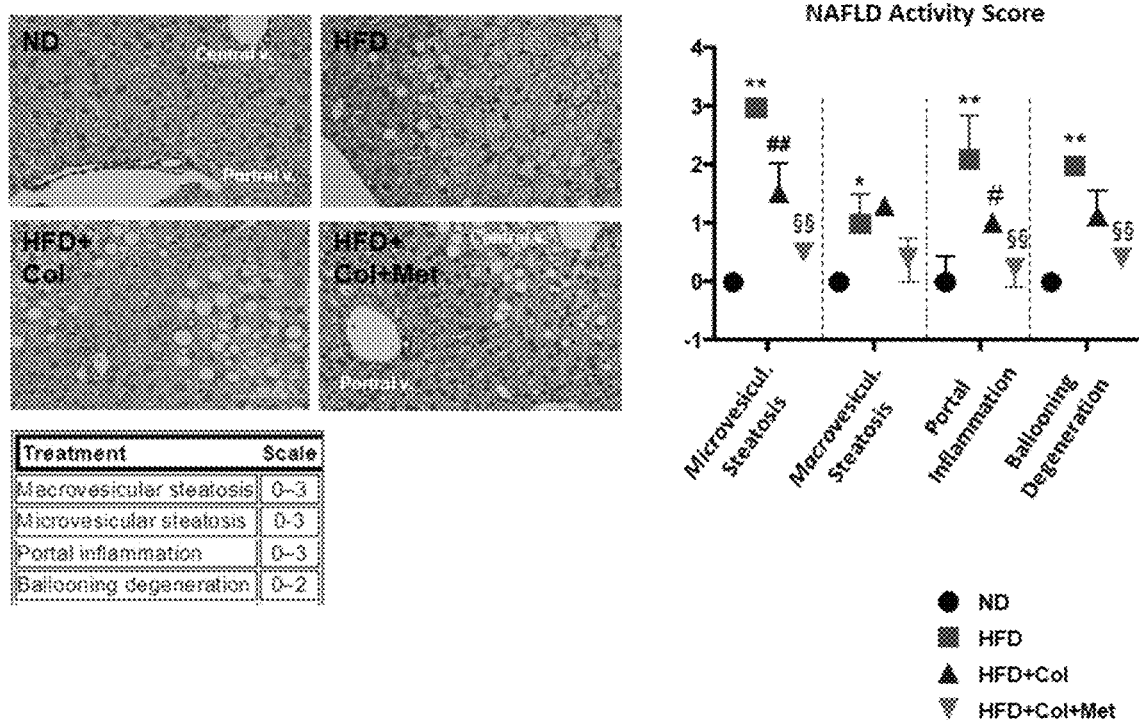
FIG. 3 shows results of a pathological test of liver tissues of rats when colchicine or colchicine/metformin was administered or co-administered to obesity-induced rats.

To perform a pathological test of the liver tissues of rats according to the administration of colchicine alone and co-administration of colchicine and metformin, histopathologic characteristics of the histologic findings for microvesicular steatosis, macrovesicular steatosis, portal inflammation, and balloon degeneration were evaluated by giving 0 point in the absence of disease (NAD), 1 point in the case of mild symptoms (Mild), 2 points in the case of moderate symptoms (Moderate), and 3 points in the case of severe symptoms (Severe), which were identified according to the severity, and the results thereof are presented in FIG. 3.

As shown in FIG. 3, it was confirmed that the microvesicular steatosis, the portal inflammation, and the ballooning degeneration were reduced by administration of colchicine alone, but there was no effect on the macrovesicular steatosis.

Tables 1 and 2 below show the results of a pathological test of the liver tissues when colchicine alone and co-administering colchicine/metformin were administered. In Table 2, the content of colchicine is 100 μg/kg.

TABLE 1

| Group | Fatty necrosis | Ballooning degeneration | Portal inflammation | Fibrosis | Total score |
|---|---|---|---|---|---|
| Normal | 0 | 0 | 0 | 0 | 0 |
| Vehicle | 0 | 0 | 0 | 0 | 0 |
| HFD | 3 | 2 | 3 | 3 | 11 |
| HFD + Colchicine (10 μg/kg) | 3 | 2 | 2 | 3 | 10 |
| HFD + Colchicine (50 μg/kg) | 2 | 2 | 2 | 2 | 8 |
| HFD + Colchicine (100 μg/kg) | 2 | 1 | 1 | 1 | 5 |
| HFD + Colchicine (200 μg/kg) | 2 | 2 | 2 | 1 | 7 |

TABLE 2

| Group | Fatty necrosis | Ballooning degeneration | Portal inflammation | Fibrosis | Total score |
|---|---|---|---|---|---|
| Normal | 0 | 0 | 0 | 0 | 0 |
| Vehicle | 0 | 0 | 0 | 0 | 0 |
| HFD | 3 | 3 | 3 | 3 | 12 |
| HFD + Colchicine | 2 | 1 | 2 | 1 | 6 |
| HFD + Colchicie + Metformin (50 mg/kg) | 2 | 1 | 2 | 1 | 6 |
| HFD + Colchicine + Metformin (100 mg/kg) | 2 | 1 | 1 | 1 | 5 |
| HFD + Colchicine + Metformin (200 mg/kg) | 1 | 1 | 1 | 1 | 4 |
| HFD + Colchicine + Metformin (400 mg/kg) | 1 | 2 | 2 | 1 | 6 |

In the case of co-administration of colchicine and metformin, enhanced effects were confirmed in comparison to administration of colchicine alone, and it was confirmed that the co-administration was able to effectively inhibit the macrovesicular steatosis.

2-2. Anatomical Change Test of Cross-Sections of Livers when Administering Colchicine Alone and Co-Administering Colchicine/Metformin to Obesity-Induced Rats For the anatomical test of the cross-sections of the livers of the rats, H&E staining was applied, and the results were shown in FIG. 4.

Figure 4:
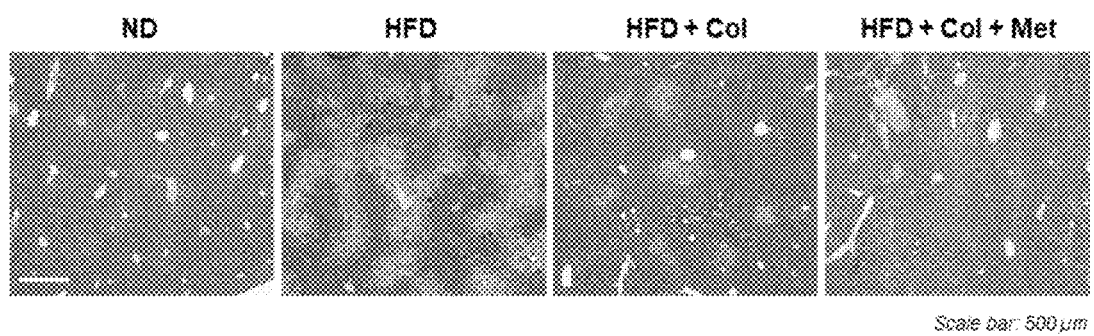
FIG. 4 shows an anatomic analysis of cross-sections of the liver of rats using H&E staining when administering colchicine or co-administering colchicine/metformin to obesity-induced rats.

As shown in FIG. 4, the high fat diet induced steatosis in the liver tissues, and from this, it was confirmed that the steatosis was reduced by administration of colchicine (100 μg/kg) alone. Furthermore, when colchicine and metformin (100 mg/kg) were co-administered, it was confirmed that a synergistic effect of the two drugs was shown, and thus the effect of reducing the steatosis was clearly shown.

Figure 5:
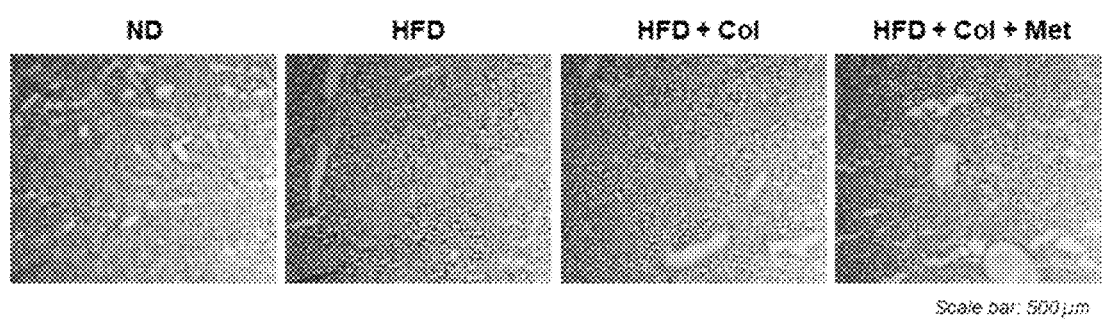
FIG. 5 shows a result of staining fats accumulated in cross-sections of the liver of rats by an oil red O method when colchicine or colchicine/metformin was administered or co-administered to obesity-induced rats.

In addition, in order to examine a quantitative change of fat accumulated in the liver tissues of the rats, the fat was confirmed by staining using an oil red O method, and the results were shown in FIG. 5.

As shown in FIG. 5, the high fat diet induced fat accumulation in the liver tissues, and it was confirmed that the fat accumulation was reduced by administration of colchicine alone. Also, it was confirmed that the effect of reducing the fat accumulation showed a synergistic effect by co-administration of colchicine/metformin.

2-3. Measurement of Activation of AMPK and ACC Metabolites in Liver Tissues of Rats when Administering Colchicine (100 μg/Kg) Alone and Co-Administering Colchicine/Metformin (100 mg/kg) to Obesity-Induced Rats Mass spectrometry was applied to confirm the above results, and the results were presented in FIG. 6.

Figure 6:
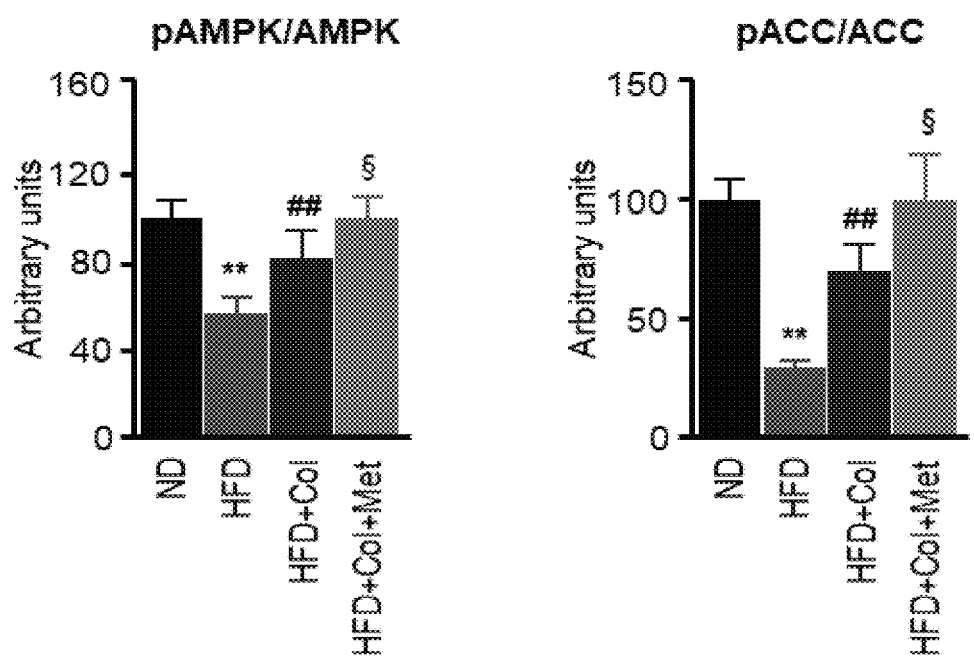
FIG. 6 shows a measurement of activation of AMPK and ACC metabolites in the liver tissues of rats using mass spectrometry when colchicine or colchicine/metformin was administered or co-administered to obesity-induced rats.

As shown in FIG. 6, activation of AMPK and ACC decreased by the high fat diet was partially recovered by administration of colchicine, and the activation of AMPK and ACC was much more increased by co-administration of colchicine/metformin. Accordingly, it was confirmed that in the combination formulation prepared by the present invention, the AMPK and the ACC were further activated by the synergistic effect of the above ingredients.

Figure 7:
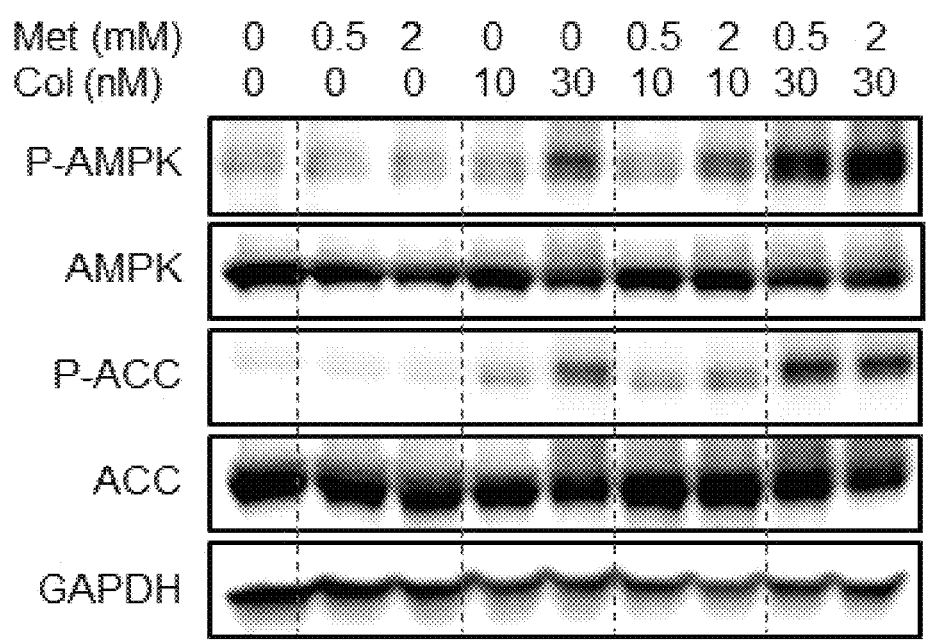
FIG. 7 shows a result of confirming whether colchicine or co-administration of colchicine/metformin affected the activation of AMPK and ACC in a hepatocyte AML12 cell line induced in the liver of rats.

In addition, the results of affecting the activation of the AMPK and ACC in a hepatocyte AML12 cell line induced in the livers of rats were further confirmed in the case of administration of colchicine alone and co-administration of colchicine/metformin, as presented in FIG. 7.

As shown in FIG. 7, it was confirmed that the activation increased by co-administration of colchicine/metformin (drug treatment for 7 hours) was more than the activation of the AMPK and ACC increased by administration of colchicine (drug treatment for 7 hours) in the rat AML12 liver cell line.

Figure 8:
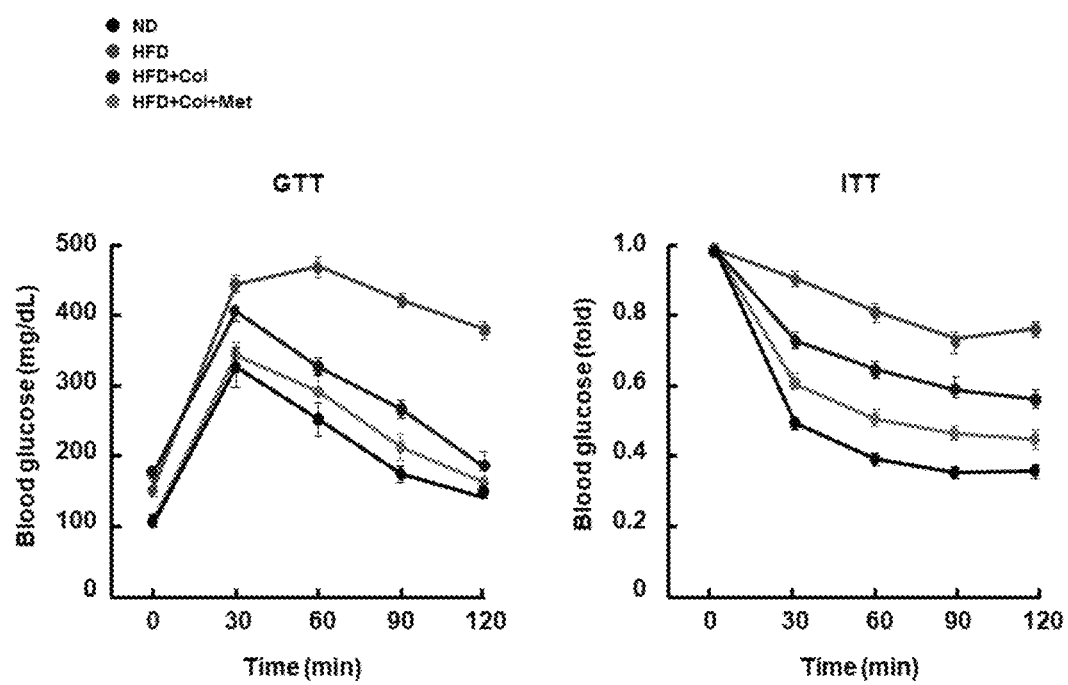
FIG. 8 is a result of a glucose tolerance test (GTT) and an insulin tolerance test (ITT) when colchicine or colchicine/metformin was administered or co-administered to obesity-induced rats.

2-4. Results of Comparing Glucose Tolerance Test (GTT) and Insulin Tolerance Test (ITT) Occurring when Administering Colchicine (100 μg/Kg) Alone or Co-Administering Colchicine/Metformin (100 mg/kg) to Obesity-Induced Rats As shown in FIG. 8, the glucose tolerance and insulin tolerance in the blood of rats with increased obesity were much more reduced by co-administration of colchicine/metformin than administration of colchicine alone.

Figure 9:
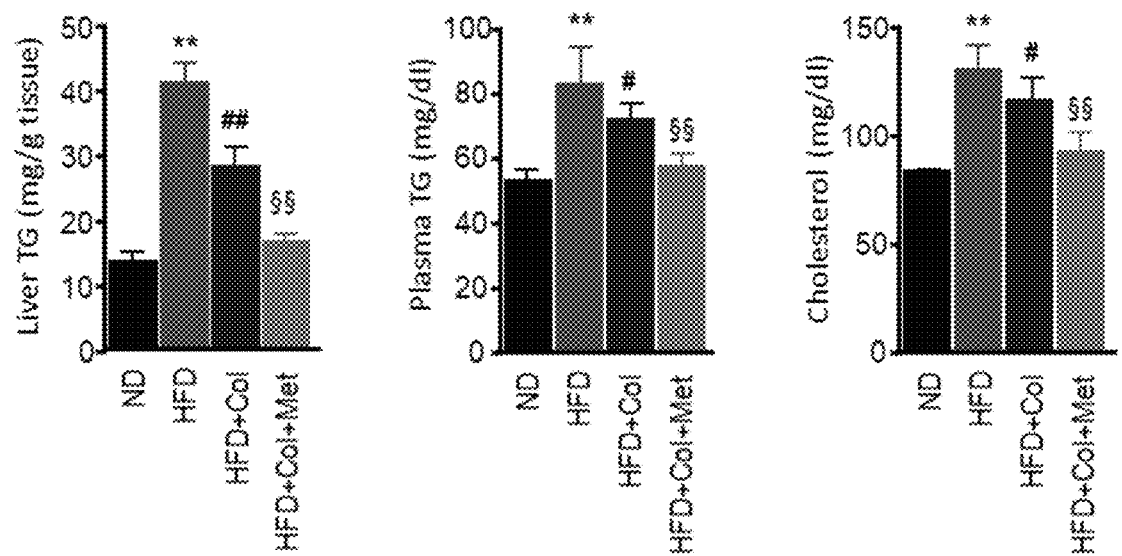
FIG. 9 shows a measurement of the levels of liver triglyceride, plasma triglyceride, and cholesterol when colchicine or colchicine/metformin was administered or co-administered to obesity-induced rats.

In addition, as can be seen from FIG. 9, the levels of liver triglyceride, plasma triglyceride, and cholesterol of the rats were much more reduced at the time of co-administration of colchicine/metformin than the administration of colchicine alone. From the above results, it can be seen that the levels of glucose tolerance, insulin tolerance, triglyceride and cholesterol are much more lowered by the synergistic effect resulting from co-administration of colchicine/metformin than the administration of colchicine alone.

Figure 10:
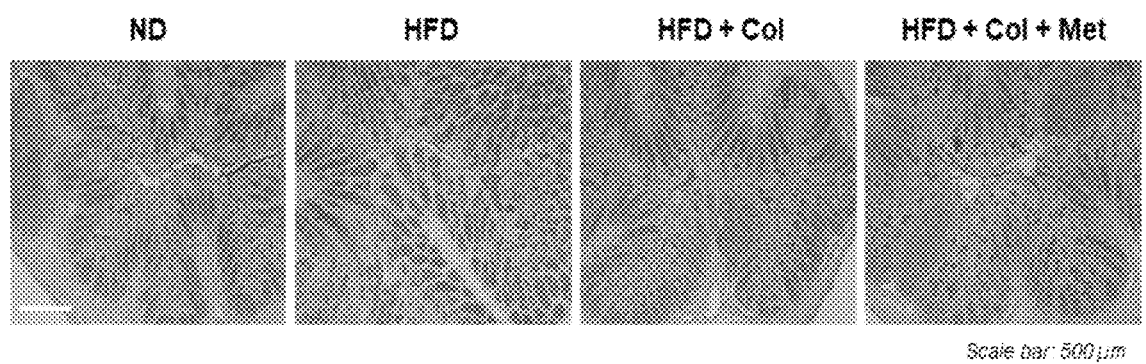
FIG. 10 shows a result of collagen staining using Masson's trichrome staining method to confirm the fibrosis of colon tissues of rats when colchicine or colchicine/metformin was administered or co-administered to obesity-induced rats.

2-5. Fibrosis Test of Colon Tissue Shown when Administering Colchicines Alone and Co-Administering Colchicine/Metformin to Obesity-Induced Rats Masson's trichrome staining was applied to confirm a difference in fibrosis of the colon tissue, and, as illustrated in FIG. 10, the fibrosis of the colon tissue of the rats is much reduced by co-administration of colchicine/metformin as compared to the administration of colchicines alone.

Table 3 below shows changes in values for a total of four items, such as albumin level, alanine aminotransferase (ALT), aspartate aminotransferase (AST), and total protein concentration occurring when colchicine alone was administered in the experiment.

TABLE 3

| Group | Albumin (g/dl) | ALT (U/L) | AST (U/L) | Total protein (g/dl) |
| --- | --- | --- | --- | --- |
| Normal | 2.33 ± 0.04 | 39.80 ± 2.65 | 88.46 ± 4.58 | 6.56 ± 0.83 |
| Vehicle | 2.32 ± 0.02 | 37.36 ± 3.05 | 88.58 ± 6.36 | 6.82 ± 0.68 |
| HFD | 1.84 ± 0.02 | 1775.28 ± 27.68 | 1802.21 ± 75.28 | 5.07 ± 0.29 |
| HFD + Colchicine (10 µg/kg) | 1.85 ± 0.01 | 1742.57 ± 102.71 | 1766.90 ± 90.48 | 5.07 ± 0.30 |
| HFD + Colchicine (50 µg/kg) | 1.98 ± 0.02 | 1602.38 ± 61.31 | 1759.49 ± 61.71 | 5.21 ± 0.33 |
| HFD + Colchicine (100 µg/kg) | 2.12 ± 0.04 | 1466.48 ± 49.34 | 1614.70 ± 78.28 | 5.24 ± 0.13 |
| HFD + Colchicine (200 µg/kg) | 1.94 ± 0.04 | 1735.40 ± 86.49 | 1833.70 ± 131.74 | 5.09 ± 0.32 |

Table 4 below shows changes in values for a total of four items, such as albumin level, ALT, AST, and total protein concentration occurring when colchicine and metformin are co-administered in the experiment. In Table 4, the content of colchicine is 100 µg/kg.

TABLE 4

| Group | Albumin (g/dl) | ALT (U/L) | AST (U/L) | Total protein (g/dl) |
| --- | --- | --- | --- | --- |
| Normal | 2.37 ± 0.03 | 38.71 ± 4.81 | 83.78 ± 5.81 | 6.31 ± 0.21 |
| Vehicle | 2.37 ± 0.03 | 37.38 ± 4.30 | 87.49 ± 12.21 | 6.83 ± 0.26 |
| HFD | 1.84 ± 0.03 | 1844.58 ± 79.80 | 1863.31 ± 113.85 | 4.56 ± 0.34 |
| HFD + Colchicine (100 µg/kg) | 2.08 ± 0.03 | 1508.64 ± 102.38 | 1574.22 ± 75.98 | 5.13 ± 0.22 |
| HFD + Colchicine + Metformin (50 mg/kg) | 2.08 ± 0.03 | 1433.21 ± 40.44 | 1391.45 ± 68.25 | 5.15 ± 0.16 |
| HFD + Colchicine + Metformin (100 mg/kg) | 2.17 ± 0.02 | 1414.24 ± 25.39 | 1297.95 ± 28.63 | 5.19 ± 0.36 |
| HFD + Colchicine + Metformin (200 mg/kg) | 2.25 ± 0.05 | 1295.65 ± 25.06 | 1068.02 ± 68.97 | 5.32 ± 0.33 |
| HFD + Colchicine + Metformin (400 mg/kg) | 2.11 ± 0.05 | 1398.16 ± 47.83 | 1248.43 ± 105.97 | 5.14 ± 0.11 |

From Tables 3 and 4, it can be seen that when colchicine and metformin are co-administered to obesity-induced rats, the activities of proteins and enzymes are maximized by the synergistic effect of the ingredients as compared to the administration of colchicine alone.

In order to confirm changes in levels of liver fibrin accumulation in obesity-induced rats that occurred when administering colchicine alone and co-administering colchicine and metformin, the changes were measured using a hydroxyproline assay, and the results were shown in Tables 5 and 6 below.

Table 5 shows changes in levels of hydroxyproline after administration of colchicine alone, and Table 6 shows changes in levels of hydroxyproline after co-administration of colchicine and metformin. In Table 6, the content of colchicine is 100 µg/kg.

TABLE 5

| Group | Hydroxyproline (µg/g of liver) |
| --- | --- |
| Normal | 248.00 ± 24.01 |
| Vehicle | 252.89 ± 20.89 |
| HFD | 355.94 ± 14.21 |
| HFD + Colchicine (10 µg/kg) | 345.28 ± 8.14 |
| HFD + Colchicine (50 µg/kg) | 326.46 ± 14.55 |
| HFD + Colchicine (100 µg/kg) | 308.13 ± 5.04 |
| HFD + Colchicine (200 µg/kg) | 324.83 ± 20.81 |

TABLE 6

| Group | Hydroxyproline (µg/g of liver) |
| --- | --- |
| Normal | 258.36 ± 15.85 |
| Vehicle | 259.20 ± 13.93 |
| HFD | 353.39 ± 19.29 |
| HFD + Colchicine (100 µg/kg) | 316.68 ± 13.36 |
| HFD + Colchicine + Metformin (50 mg/kg) | 306.81 ± 10.67 |
| HFD + Colchicine + Metformin (100 mg/kg) | 291.14 ± 15.34 |
| HFD + Colchicine + Metformin (200 mg/kg) | 268.89 ± 10.52 |
| HFD + Colchicine + Metformin (400 mg/kg) | 277.23 ± 16.33 |

As can be seen from Examples described above, the combination formulation of colchicine and metformin provided in exemplary embodiments of the present invention can be an excellent pharmaceutical composition capable of treating various liver diseases such as liver hepatitis, liver cirrhosis, etc, by preventing the accumulation of fat tissues in a living body by a synergistic effect of the above ingredients and reducing glucose tolerance and insulin tolerance.

In addition, because the pharmaceutical composition provided in exemplary embodiments of the present invention does not use ursodeoxycholic acid, which has been mainly used in the related art for treatment and prevention of liver disease, the pharmaceutical composition according to embodiments of the present invention can be a useful pharmaceutical composition capable of replacing ursodeoxycholic acid, given the fact that almost all ursodeoxycholic acid raw materials are imported from China.

The aforementioned description of the present invention is only exemplary, and it will be understood by those skilled in the art that the technical spirit or required features of the present invention can be easily modified in other specific forms. Therefore, it should be appreciated that the embodiments described above are all illustrative in all aspects and are not restricted.

The invention claimed is:

1. A pharmaceutical composition for treatment of liver disease comprising colchicine and metformin,
    wherein a content of colchicine contained in the pharmaceutical composition is 10 to 100 μg/kg, and a content of metformin is 100 to 200 mg/kg, and
    wherein the liver disease is at least one selected from liver fibrosis, liver cirrhosis, alcoholic hepatitis, and non-alcoholic hepatitis.

2. The pharmaceutical composition for treatment of liver disease of claim 1, wherein the pharmaceutical composition is prepared in at least one formulation selected from the group consisting of powders, granules, tablets, capsules, suspensions, emulsions, syrups, aerosols, external preparations, suppositories, and injection solutions.

3. The pharmaceutical composition for treatment of liver disease of claim 1, wherein the pharmaceutical composition further comprises at least one ingredient selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc and magnesium stearate.

4. The pharmaceutical composition for treatment of liver disease of claim 1, wherein the pharmaceutical composition further comprises at least one ingredient selected from the group consisting of thiamine, riboflavin, niacin, pantofenic acid, pyridoxine, cobalamin, vitamin C, vitamin D, vitamin E, and N-acetylcysteine.

5. A pharmaceutical composition for enhancing therapy of liver disease comprising colchicine and metformin,
    wherein a content of colchicine contained in the pharmaceutical composition is 10 to 100 μg/kg, and a content of metformin is 100 to 200 mg/kg, and
    wherein the liver disease is at least one selected from liver fibrosis, liver cirrhosis, alcoholic hepatitis, and non-alcoholic hepatitis.

6. The pharmaceutical composition for enhancing the therapy of liver disease of claim 5, wherein the pharmaceutical composition is prepared in any one formulation selected from the group consisting of powders, granules, tablets, capsules, suspensions, emulsions, syrups, aerosols, external preparations, suppositories, and injection solutions.

7. The pharmaceutical composition for enhancing the therapy of liver disease of claim 5, wherein the pharmaceutical composition further comprises at least one ingredient selected from the group consisting of lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc and magnesium stearate.

8. The pharmaceutical composition for enhancing the therapy of liver disease of claim 5, wherein the pharmaceutical composition further comprises at least one ingredient selected from the group consisting of thiamine, riboflavin, niacin, pantothenic acid, pyridoxine, cobalamin, vitamin C, vitamin D, vitamin E, and N-acetylcysteine.

* * * * *